United States Patent [19]
Powell

[11] Patent Number: 4,743,240
[45] Date of Patent: May 10, 1988

[54] DISPOSABLE DIAPER SYSTEM
[75] Inventor: Monica Powell, Takoma, Wash.
[73] Assignee: Robert Dohlke, Spanaway, Wash.
[21] Appl. No.: 8,755
[22] Filed: Jan. 30, 1987
[51] Int. Cl.⁴ ............................................. A61F 13/16
[52] U.S. Cl. ................................................ 604/385 R
[58] Field of Search ................... 604/385.1, 385.2, 386, 604/358

[56] References Cited
U.S. PATENT DOCUMENTS

| | | | |
|---|---|---|---|
| 3,369,545 | 2/1968 | Wanberg | 604/385.1 |
| 3,865,110 | 2/1975 | Traverse | 604/385.1 |
| 3,920,019 | 11/1975 | Schaar | 604/385.1 |
| 4,085,753 | 4/1978 | Gellert | 604/385.1 |
| 4,221,221 | 9/1980 | Ehrlich | 604/386 |

Primary Examiner—John D. Yasko
Attorney, Agent, or Firm—Leonard Bloom

[57] ABSTRACT

A diaper system for a baby including a diaper formed substantially as a rectangular blank having tabs at the corners and leg engaging areas along the longitudinal aspects including elastic, a plurality of pockets contained on the diaper integrally therewith carrying medicaments used in baby hygiene, and a bag integrally formed with the diaper adapted to be inverted to encapsulate a soiled diaper within what had heretofore been an interior portion of the bag. A separate container is associated with plural diapers for storage of both clean and soiled diapers.

18 Claims, 1 Drawing Sheet

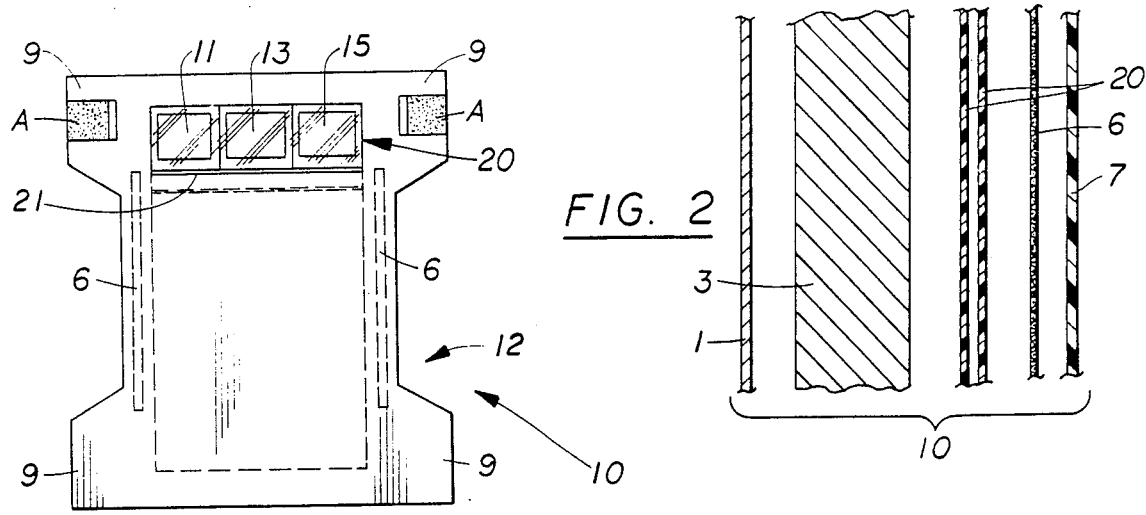
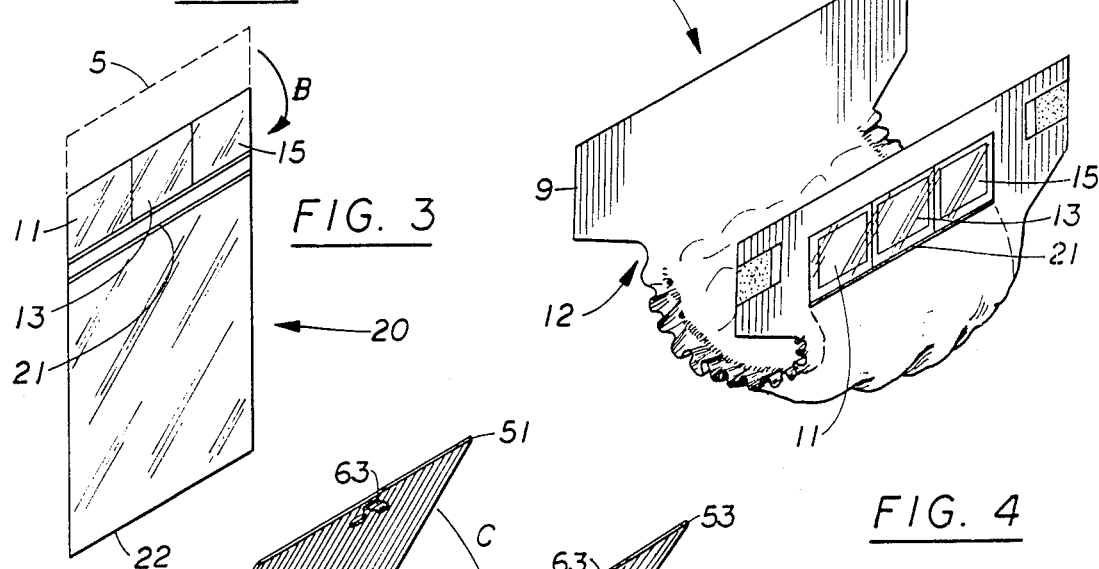
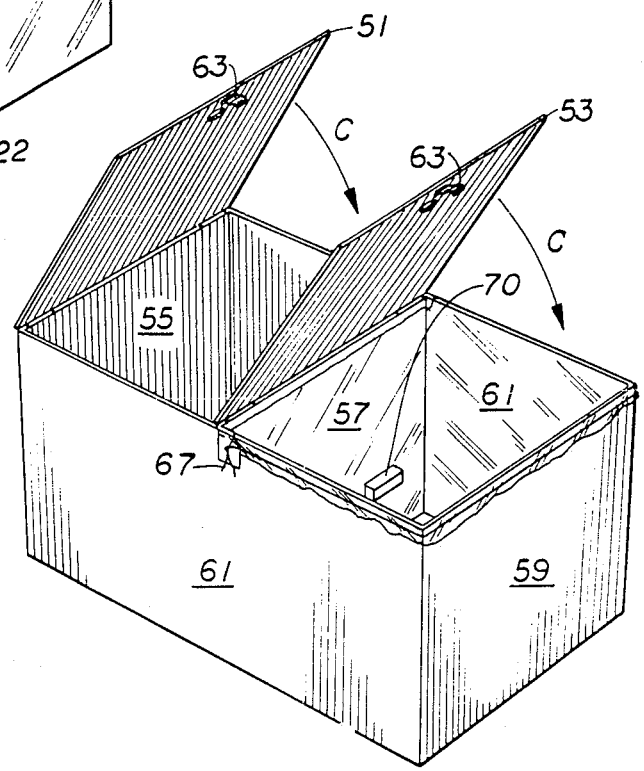

DISPOSABLE DIAPER SYSTEM

FIELD OF THE INVENTION

The following invention relates to a system for use, storage and disposal of baby diapers which renders clean, fresh diapers readily accessible, and disposes of soiled ones with a minimal amount of bother and foul odors. The system includes instrumentalities to be used with the baby to facilitate clean-up, while reducing the chance of the baby getting a rash.

BACKGROUND OF THE INVENTION

Proper baby hygiene is an important aspect in raising a child. Since a baby will soil diapers on a fairly frequent basis, disposable diapers have come into vogue as a convenient means for discharging this chore. However, most diapers currently on the market which are disposable are not readily accepted by the sewer system. Moreover, they do not provide adequate means for cleansing the baby during changing to remove human waste which has come in contact with the baby's skin.

Thus, one in charge of baby maintenance frequently must carry a plurality of accessories for the child's hygiene. Heretofor a comprehensive system or kit has not been provided.

SUMMARY OF THE INVENTION

The instant invention is distinguished over prior art as exemplified in grocery stores and marketed by large corporations. An absorbent blank of material serving as a diaper is provided, of substantially rectangular configuration and having tab members at corners of the blank. These tab members facilitate fastening of the diaper about the baby. A leg portion is provided between the tabs that includes an elastic band to facilitate proper engagement of the diaper with respect to the baby.

The diaper itself is formed from a plurality of layers. The layer which is closest to the baby is formed from paper. Next there are a plurality of absorbent layers, and finally a plastic outer layer.

One unique feature of the invention interposes an open ended bag between the absorbent layers and plastic outer layer. The bag has a slit or opening through the plastic outer layer allowing access to its interior. A flap associated with the bag exposes a plurality of pockets adjacent the mouth of the bag, and the various pockets contain therein towelettes specially treated for the purposes of promulgating baby hygiene and powder to minimize the possibility that an ammonia rash can occur on the baby.

The bag formed integrally with the diaper allows placement of the soiled diaper there within the bag, allowing the bag to completely encapsulate the soiled diaper for storage prior to disposal.

In one form of the invention, a two-enclosure container is included having a plurality of clean, unsoiled diapers in a first enclosure, and adjacent thereto, a second enclosure for reception therein of the soiled diapers once inverted and encapsulated by the bag. The section of the container which receives the soiled diapers includes a plastic liner which will slide from the container for convenient removal and subsequent placement into an appropriate trash second enclosure which receives the soiled diapers) for sanitizing the air.

OBJECTS OF THE INVENTION

Accordingly, it is a primary object of this invention to provide a new and novel diaper.

In addition, it is a further object of this invention to provide an associated container to be used with the new and novel diaper thereby defining a kit which facilitates the process associated with changing a baby's diapers.

It is yet a further object of this invention to provide a device as characterized above which carries integrally with the diaper a plurality of medicaments for treating the baby and removing human waste from the baby while changing the diaper.

It is a further object of this invention to provide a device as characterized above which includes an integrally formed bag associated with the diaper so that a soiled diaper can be stored within the bag by placing one's hand within the bag, grasping the diaper around a crotch area, and finally pulling the soiled diaper within the bag, inverting the bag so that a previously interior portion of the bag is now exteriorly disposed. In one form of the invention, it is an object to provide a locking mechanism along the opening of the bag to seal the used diaper there within.

It is yet a further object of this invention to provide a device as characterized above which provides for the storage of fresh and used diapers in such a way that transport of a plurality of same is feasible. To this end, a deodorizer is placed in an enclosure of the container carrying the soiled diapers for air freshening.

A further object of this invention contemplates providing a device as characterized above which is extremely durable in construction and is capable of being mass produced competively with existing commercial products.

A further object of this invention includes providing a device as characterized above which enhances baby hygiene.

It is a further object of this invention to provide a diaper for use with babies, toddlers or the like, comprising in combination a substantially rectangular blank having tab portions at corners thereof whereby parallel lines between adjacent tab portions define longitudinal and latitudinal edges thereof, two longitudinal edges having a narrowed area provided with an elastic edge so as to accommodate the leg area of the baby, and said latitudinal edges oriented to circumscribe the waist area of a baby said rectangular blank formed from a plurality of layers including an absorbent layer and a plastic outer layer and a protective bag integrally formed with said diaper whereby an interior of said bag can be grasped by a person changing said diaper and the entire diaper can be pulled within said bag thereby inverting said bag to totally encapsulate a soiled diaper.

A further object of this invention is to provide a device wherein said diaper bag has an interior and an exterior, and said exterior is interposed between said absorbent layer and said plastic outer layer, and said bag interior when inverted encapsulates the entire diaper.

It is yet a further object of this invention to provide a diaper wherein said diaper has a paper inner layer immediately adjacent the baby when the baby wears said diaper.

A further object of this invention is to provide a diaper including a plurality of pockets carried on said diaper each having medicaments disposed therein whereby when a baby has soiled a diaper and is to be changed with a new diaper, each of said pockets carrying a medicament can be accessed and said medicament can be used to clean the baby.

A further object of this invention is to provide a device wherein three said pockets are provided.

A further object of this invention is to provide a device wherein said pockets are integrally formed with said bag, and disposed above an opening of said bag, said pockets are provided with an overlying flap to selectively expose access to the interior contents of each said pocket whereby the baby does not have direct access to said pockets.

It is an object of this invention to provide a diaper wherein the improvement comprising a plurality of pockets contained on the diaper each having medicaments disposed therein whereby when a baby has soiled a diaper and is to be changed with a new diaper, each of said pockets carrying a medicament can be accessed and said medicaments can be used to clean baby.

It is a further object of this invention to provide a device wherein three said pockets are provided, said pockets are integrally formed with said bag, and disposed above an opening of said bag, said pockets are provided with an overlying flap to selectively expose access to the interior contents of each said pocket whereby the baby does not have direct access to the pockets.

It is a further object of this invention to provide a device wherein each medicament is in the form of a towelette, one having a mild detergent and one having a lubricant.

It is yet a further object of this invention to provide a device including a further pocket having a powder packet contained there within.

It is a further object of this invention to provide a device including a bag integrally formed with said diaper including an opening providing sealing means, whereby said bag can be used to store a sole diaper therein by placing one's hand within an interior of said bag and inverting said bag to encapsulate the diaper there within.

It is a further object of this invention to provide a device including a storage container for both used and new diapers including an open ended box having a partitioned wall medially disposed therebetween and first and second doors associated one with each said compartment, one compartment to receive clean, unsoiled diapers, and said second compartment including a bag liner and deodorizing means to receive soiled diapers there within.

It is an object of this invention to provide a method for attending to baby hygiene including the steps of removing a soiled diaper from the baby, accessing medicaments from within pockets carried on a fresh diaper including applying a towelette on the baby having a mild detergent thereon, applying thereafter a lubricant on the baby, applying thereafter a baby powder thereon, attaching the new diaper onto the baby by orienting the baby so that the baby's legs pass over leg engaging elastic areas of the diaper, engaging tab members on a front portion of the diaper so as to gird the baby and taking the soiled diaper, extending a person's hand into a pocket formed on the soiled diaper and inverting the bag such that a heretofore interior of the bag is now exterior and pulling the contents of the soiled diaper including the diaper within the bag.

These and other objects will be made manifest when considering the following detailed description when taken in conjunction with the appended drawing figures.

BRIEF DESCRIPTION OF THE DRAWING FIGURES

FIG. 1 is a plan view of the apparatus according to the present invention.

FIG. 2 is a side view of the components associated with a portion of the diaper shown in FIG. 1 expanded for clarity.

FIG. 3 is a perspective view of the bag associated with the present invention.

FIG. 4 shows the diaper in an orientation to conform with the anatomy of a baby.

FIG. 5 is a perspective view of the container which houses both new and used diapers.

BRIEF DESCRIPTION OF THE PREFERRED EMBODIMENT

Referring to the drawings now, wherein like reference numerals refer to like parts throughout the various drawing figures, reference numeral 10 is directed to the diaper assembly according to the present invention.

As shown in FIG. 1, the diaper 10 is formed from a substantially rectangular blank having tab portions 9 at corners of the blank. Areas 12 between two longitudinal aspects of the tabs 9 can accomodate a baby's legs. See FIG. 4 for example. The area adapted to accomodate a baby's legs includes an elastic 6 sewn within the diaper so that when the baby inevitably soils himself, a high degree of containment is provided.

As shown in FIG. 2, the diaper 10 is formed from a paper inner layer 1 placed adjacent the baby. Next absorbent layers 3 are further removed from the baby. A bag 20 is provided beyond layer 3 and finally a plastic outer layer 7.

Attention is now directed to FIG. 3 which shows certain features with respect to the bag 20 integrally formed with the diaper 10. As shown, a bag flap 5 is provided which moves from a first to a second position as suggested by the arrow B to either expose or occlude a plurality of pockets 11, 13, 15. When the flap is in the open position, these three pockets preferrably contain: two towelettes containing a mild cleansing agent in pocket 15, a towelette containing a lubricating agent such as petroleum jelly 13, and a packet containing powder to be stored in pocket 11.

Directly below the plurality of pockets 11, 13, 15, a slit opening 21 is provided to allow access to the interior to the bag 20, which (as shown in FIG. 3) extends downwardly and (as shown in FIG. 4) girds substantially the entire crotch portion of the baby.

Assume that the diaper of FIG. 1 has had the contents of the various pockets utilized in the diaper changing process. Adhesive strips A contained on the tabs 9 can be used to gird the clean diaper on the baby until it is time for the next changing. When changing the baby, the old diaper is removed, and the hand of the person performing the diaper change is placed in the slit 21 of the bag 20 extending downwardly to the bottom edge 22 shown in FIG. 3. When thusly placed, the entire contents of the diaper can be pulled into the bag by grasping the diaper through the bag and inverting the bag. What had heretofor been the interior of the bag now encloses the entire diaper 10. Various and appropriate means for sealing the opening 21 of the bag 20 can be now effected as is well known in the art.

Attention is now directed to FIG. 5 which shows a container 100 when the diaper and container assembly is to be used as a kit.

The container 100 is a five sided box having side walls 55, 59, 61 and a bottom wall (not shown). A partition 57 separates the container into two enclosure type compartments. One compartment is intended to receive clean diapers for storage and removal as needed, and the second compartment is intended to receive soiled diapers there within. For this purpose, a bag liner 65 is contained within the second compartment and serves as the storage area for the dirty diapers. The liner includes a turned over lip which nests on a top edge of the side walls 57, 59 and 61. Each compartment of the container 100 includes a hinged lid 51, 53 and further is provided with a latch mechanism 63 for convenience in opening and closing the container.

The bag liner 65 may be of the type having a draw string along a top periphery thereof to draw the bag liner 65 tightly closed when disposing of a plurality of dirty diapers en masse. A deodorant 70 is shown in the dirty diaper container to minimize whatever odors may emanate therefrom.

Having thus described the invention, it should be apparent that numerous structural modifications and adaptations may be resorted to without departing from the fair meaning, scope and spirit of the application as defined hereinabove and as claimed hereinbelow.

I claim:

1. A diaper for use with babies, toddlers or the like comprising in combination:
    a substantially rectangular blank having tab portions at corners thereof whereby parallel lines between adjacent tab portions define longitudinal and latitudinal edges thereof, two longitudinal edges having a narrowed area provided with an elastic edge so as to accommodate the leg area of the baby, and said latitudinal edges oriented to circumscribe the waist area a baby,
    said rectangular blank formed from a plurality of layers including an absorbent layer and a plastic outer 1
    and a protective bag integrally formed with said diaper whereby an interior of said bag can be grasped by a person changing said diaper and the entire diaper can be pulled within said bag thereby inverting said bag to totally encapsulate a soiled diaper, wherein said diaper bag has an interior and an exterior, and said exterior is interposed between said absorbent layer and said plastic outer layer, and said bag interior when inverted encapsulates the entire diaper.

2. The diaper of claim 1 wherein said diaper has a paper inner layer immediately adjacent the baby when the baby wears said diaper.

3. The diaper of claim 2 including a plurality of pockets carried on said diaper each having medicaments disposed therein whereby when a baby has soiled a diaper and is to be changed with a new diaper, each of said pockets carrying a medicament can be accessed and said medicament can be used to clean the baby.

4. The device of claim 3 wherein three said pockets are provided.

5. The device of claim 4 wherein said pockets are integrally formed with said bag, and disposed above an opening of said bag, said pockets are provided with an overlying flap to selectively expose access to the interior contents of each said pocket whereby the baby does not have direct access to said pockets.

6. In a diaper, the improvement comprising a plurality of pockets contained on the diaper, each having medicaments disposed therein, whereby when a baby has soiled a diaper and is to be changed with a new diaper, each of said pockets carrying a medicament can be accessed and said medicaments can be used to clean the baby, and a protective bag integrally formed with said diaper, whereby an interior of said bag can be grasped by a person changing said diaper and the entire diaper can be pulled with said bag, thereby inverting said bag totally encapsulate a soiled diaper, wherein said diaper bag has an interior and an exterior, and said exterior is interposed between said absorbent layer and said plastic outer layer, and said bag interior when inverted encapsulates the entire diaper.

7. In a diaper, the improvement comprising a plurality of pockets contained on the diaper, each having medicaments disposed therein, whereby when a baby has soiled a diaper and is to be changed with a new diaper, each of said pockets carrying a medicament can be accessed and said medicaments can be used to clean the baby, wherein three said pockets are provided, said pockets are integrally formed with a bag, and disposed above an opening of said bag, said pockets are provided with an overlying flap to selectively expose access to the interior contents of each said pocket, whereby the baby does not have direct access to the pockets.

8. The device of claim 7 wherein each medicament is in the form of a towelette, one having a mild detergent and one having a lubricant.

9. The device of claim 8 including a further pocket having a powder packet contained there within.

10. The device of claim 9 including a bag integrally formed with said diaper including an opening providing sealing means, whereby said bag can be used to store a sole diaper therein by placing one's hand within an interior of said bag and inverting said bag to encapsulate the diaper there within.

11. The device of claim 10 including a storage container for both used and new diapers including an open ended box having a partitioned wall medially disposed therebetween and first and second doors associated one with each said compartment, one compartment to receive clean, unsoiled diapers, and said second compartment including a bag liner and deodorizing means to receive soiled diapers there within.

12. A diaper for use with babies, toddlers or the like, comprising in combination:
    a substantially rectangular blank having tab portions at corners thereof, whereby parallel lines between adjacent tab portions define longitudinal and latitudinal edges thereof, two longitudinal edges having a narrowed area provided with an elastic edge so as to accommodate the leg area of the baby, and said latitudinal edges oriented to circumscribe the waist area of a baby, said rectangular blank formed from a plurality of layers including an absorbent layer and a plastic outer layer,
    a protective bag integrally formed with said diaper, wherein the entire diaper can be placed within said bag to totally encapsulate a soiled diaper, wherein said diaper bag has an interior layer and an exterior layer, and said interior layer is located between said absorbent layer and said plastic outer layer.

13. In a disposable diaper for use with babies, toddlers or the like, the diaper including sides for accommodating the baby's legs and including sides for accommodating the baby's waist, the diaper including a plurality of layers including an absorbent layer and a plastic outer layer, the improvement comprising:

a protective bag integrally formed with said diaper, whereby an interior of said bag can be grasped by a person changing said diaper and the entire diaper can be pulled within said bag, thereby inverting said bag to totally encapsulate a soiled diaper, wherein said diaper bag has an interior and an exterior, and said exterior is interposed between said absorbent layer and said plastic outer layer, and said bag interior when inverted encapsulates the entire diaper.

14. In a disposable diaper, the improvement comprising at least one pocket contained on the diaper and having a cleaning article disposed therein, whereby when a baby has soiled the diaper and is to be changed with a new diaper, said pocket carrying the cleaning article can be accessed and said cleaning article can be used to clean the baby, wherein said pocket is integrally formed with a disposable bag, and wherein said pocket is located above an access opening of said bag.

15. The disposable diaper of claim 14, wherein said pocket is provided with an overlying flap to selectively expose access to the interior contents of said pocket, whereby the baby does not have direct access to the pocket.

16. In a disposable diaper for use with babies, toddlers or the like, the diaper including sides for accommodating the baby's legs and including sides for accommodating the baby's waist, the diaper including a plurality of layers including an absorbent layer and a plastic outer layer, the improvement comprising:

a protective bag integrally formed with said diaper whereby an interior of said bag can be grasped by a person changing said diaper and the entire diaper can be pulled within said bag, thereby inverting said bag to totally encapsulate a soiled diaper, wherein said diaper bag has an interior and an exterior, and said exterior is interposed between said absorbent layer and said plastic outer layer, and said bag interior when inverted encapsulates the entire diaper, and at least one pocket contained on the diaper having a cleaning article disposed therein, whereby when a baby has soiled the diaper and is to be changed with a new diaper, said pocket carrying the cleaning article can be accessed and said cleaning article can be used to clean the baby.

17. A diaper for use with babies, toddlers or the like, comprising in combination:

a substantially rectangular blank having tab portions at corners thereof whereby parallel lines between adjacent tab portions define longitudinal and latitudinal edges thereof, two longitudinal edges having a narrowed area so as to accommodate the leg area of the baby, and said latitudinal edges oriented to circumscribe the waist area of a baby, said rectangular blank formed from a plurality of layers including an absorbent layer and a plastic outer layer, and a protective bag integrally formed with said diaper, whereby an interior of said bag can be grasped by a person changing said diaper and the entire diaper can be pulled within said bag thereby inverting said bag to totally encapsulate a soiled diaper, wherein said diaper bag has an interior and an exterior, and said exterior is interposed between said absorbent layer and said plastic outer layer, and said bag interior when inverted encapsulates the entire diaper.

18. A diaper for use with babies, toddlers or the like, comprising in combination:

a substantially rectangular blank having tab portions at corners thereof whereby parallel lines between adjacent tab portions define longitudinal and latitudinal edges thereof, two longitudinal edges having a narrowed area provided with an elastic edge so as to accommodate the leg area of the baby, and said latitudinal edges oriented to circumscribe the waist area of a baby, said rectangular blank formed from a plurality of layers including an absorbent layer and a plastic outer layer, a protective bag integrally formed with said diaper, whereby an interior of said bag can be grasped by a person changing said diaper and the entire diaper can be pulled within said bag, thereby inverting said bag to totally encapsulate a soiled diaper, wherein said diaper bag has an interior and an exterior, and said exterior is interposed between said absorbent layer and said plastic outer layer, and said bag interior when inverted encapsulates the entire diaper, and at least one pocket contained on the diaper and having a cleaning article disposed therein, whereby when a baby has soiled the diaper and is to be changed with a new diaper, said pocket carrying the cleaning article can be accessed and said cleaning article can be used to clean the baby, wherein said pocket is integrally formed with a disposable bag, and wherein said pocket is located above an access opening of said bag, said pocket provided with an overlying flap to selectively expose access to the interior contents of said pocket, whereby the baby does not have direct access to the pocket.

* * * * *